US007223609B2

(12) United States Patent
Anvar et al.

(10) Patent No.: US 7,223,609 B2
(45) Date of Patent: May 29, 2007

(54) ARRAYS FOR MULTIPLEXED SURFACE PLASMON RESONANCE DETECTION OF BIOLOGICAL MOLECULES

(75) Inventors: David Anvar, Sunnyvale, CA (US); Heidi Linch Reynolds, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 478 days.

(21) Appl. No.: 10/641,515

(22) Filed: Aug. 14, 2003

(65) Prior Publication Data

US 2005/0037365 A1 Feb. 17, 2005

(51) Int. Cl.
*G01N 21/03* (2006.01)
*C12M 1/34* (2006.01)
*C12Q 1/68* (2006.01)
*C12M 1/00* (2006.01)
*B32B 5/02* (2006.01)
*G01N 33/53* (2006.01)

(52) U.S. Cl. .................. 436/165; 436/164; 422/50; 422/55; 422/58; 422/60; 422/82.05; 435/6; 435/7.1; 435/287.2

(58) Field of Classification Search .................. None
See application file for complete search history.

(56) References Cited

U.S. PATENT DOCUMENTS 5,007,708 A * 4/1991 Gaylord et al. ............. 359/569
5,313,264 A * 5/1994 Ivarsson et al. ............... 356/73
5,738,825 A * 4/1998 Rudigier et al. ......... 422/82.11
5,769,074 A * 6/1998 Barnhill et al. ............. 600/300
6,057,587 A * 5/2000 Ghandehari et al. ........ 257/437
6,312,913 B1 * 11/2001 Wang et al. .................... 435/6
6,329,209 B1 * 12/2001 Wagner et al. ............... 436/518
6,458,543 B1 * 10/2002 Gold et al. ...................... 435/6
2001/0026943 A1 * 10/2001 Dickopf et al. ............. 436/164
2002/0058273 A1 * 5/2002 Shipwash ....................... 435/6
2002/0095073 A1 * 7/2002 Jacobs et al. ................ 600/300

* cited by examiner

*Primary Examiner*—Jill Warden
*Assistant Examiner*—Neil Turk (57) ABSTRACT

Arrays are provided for multiplexed evanescent scanning by allowing for high-contrast Surface Plasmon Resonance images thereof. The arrays target features are typically biopolymeric in nature, though they may be any sort of chemical or ligand. The type of scanning is such that there is no need for probe labeling. As no labeling is required, a broader range of applications than otherwise possible is facilitated. In the subject arrays, target features are set upon a noble metal film deposited on a substrate. Interfeature areas are adapted to trap, divert and/or bleed-away light so that light directed through the substrate will not be reflected by those areas and interfere with evanescent scanning of the reflective areas upon which intended target features are provided. Geometric and materials-based light attenuating features are contemplated. Arrays as described, hardware and software as required for reading such arrays, and associated methodology are covered.

16 Claims, 3 Drawing Sheets

ARRAYS FOR MULTIPLEXED SURFACE PLASMON RESONANCE DETECTION OF BIOLOGICAL MOLECULES

FIELD OF THE INVENTION

This invention relates to chemical or ligand array scanning and, more particularly, to evanescent scanning of biopolymer arrays by Surface Plasmon Resonance (SPR) analysis.

BACKGROUND OF THE INVENTION

Pharmaceutical, biotechnology, or genomics companies use DNA analysis systems for target identification and drug screening in pharmaceutical drug discovery. In many of these systems, biomolecules (e.g., DNA, RNA, cDNA, proteins) labeled with various dyes bind to chips that offer different molecular probe counterparts for binding in different locations of the chip. An optical scanner is then used to read the fluorescence of these resultant surface bound molecules under illumination with suitable (most often laser) light. Another type of detection for arrays involves the use of multiple electrode elements patterned with various biological molecules on the surface to detect analytes labeled with electrochemically active probes. A third array method operates by optical detection of semiconductor nanopartices attached to biological molecules.

Another mode of scanning is presented in U.S. Pat. No. 5,633,724. As with the other modes of detection noted above, the method taught in the patent requires that probes be attached to the biological molecules of interest. In the case of the '724 patent, fluorescent labeling is used. In contrast to the aforementioned fluorescence-based detection technique, however, this approach employs evanescent excitation of tags or labels instead of direct illumination of the same.

Evanescence involves a situation where incident light is totally reflected off of a surface, but the electromagnetic field component penetrates a short distance (tens of nanometers) into an adjacent medium While many array-based studies of bioaffinity interactions employ fluorescently labeled biopolymers, there is a recognized need for the continued development of sensitive analytical methods that can be used to detect bioaffinity interactions in biological samples without the need of molecular labels or tags. This is especially true for the case of protein-protein interactions, where labeling is difficult and can interfere with protein function.

SPR imaging is used today to detect the presence of a biopolymer on a chemically modified gold surface by the change in the local index of refraction that occurs upon adsorption. Conventional implementations of SPR analysis involve only one element (one region over which detection is measured) or 3–5 elements in a parallel arrangement at most. However, such systems are not amenable to carrying out high-throughput methodologies.

SUMMARY OF THE INVENTION

Embodiments in accordance with the invention offer a different approach, particularly with respect to the manner of image resolution for detecting array feature data. Embodiments in accordance with the invention operate to obtain SPR image data without the need for a post-reflectance filter and/or a rotational stage to improve image contrast. As a consequence, embodiments in accordance with the invention offer an advance in ease (and potentially accuracy) in multiplexed SPR implementation over any known system. In addition, other benefits, advantages and distinguishing features may be apparent to those with skill in the art upon review of the following discussion regarding embodiments in accordance with the invention.

In a similar vein, it is to be understood that while the embodiments in accordance with the invention are discussed in terms of typical array use, the "arrays" provided may be employed in other settings including that of microfluidics (e.g., as in "Lab-on-a-Chip" applications), diagnostic applications and others.

BRIEF DESCRIPTION OF THE DRAWINGS

Each of the following figures diagrammatically illustrates aspects of the invention. To facilitate understanding, the same reference numerals have been used (where practical) to designate similar elements that are common to the figures.

DEFINITIONS

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer/polymer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

An "array," includes any two-dimensional or substantially two-dimensional arrangement of addressable regions bearing a particular chemical moiety or moieties (e.g., biopolymers such as polynucleotide sequences (nucleic acids), polypeptides (e.g., proteins), etc.) associated with that region. In the broadest sense, typical arrays are arrays of ligand or chemical (e.g., polymeric or biopolymeric) polymeric binding agent features, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g., the 3' or 5' terminus). Sometimes, the arrays are arrays of polypeptides (e.g., proteins) or fragments thereof.

Any given substrate may carry one, two, four or more arrays disposed on a front surface of the substrate. The "substrate" is a material, (e.g., a dielectric material) that permits transmission to such light as desired to be used in the subject SPR analysis. Substrates in accordance with the invention may include not only regions supporting array features set upon the same, but also the light-attenuating features described in detail below. The substrate is typically made of a material that emits low fluorescence upon illumination with the light. Highly transparent materials are typically used so as to reduce the absorption of the incident illumination to improve detection of light reflected through the substrate as well as to avoid substrate heating. Generally, the substrate will transmit at least 85%, 90%, or 95%, of the illuminating light incident on the front as may be measured across the entire integrated spectrum of such illuminating light or alternatively at selected wavelengths of visible light or from infrared or UV light sources. Suitable substrate materials include: glass, quartz and/or selected polymers (depending on desired wavelength(s) of light). One suitable polymer is polyphenyl. Still, glass or quarts material may be used.

Depending upon the use, any or all of the arrays may be the same or different from one another and each may contain multiple spots or features. A typical array may contain more than ten, more than one hundred, more than one thousand, more than ten thousand features, or even more than one hundred thousand features, in an area of less than 20 cm$^2$ or even less than 10 cm$^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will be provided, such as elaborated upon below. It will be appreciated, that the interfeature areas may, of course, be of various sizes and configurations so long as they adhere to the principles of operation discussed or implicit to the structures discussed below. More generally, however, it is noted that the interfeature areas or array features themselves may represent a perfectly repeating or periodic pattern. Alternatively, variation in the structures is possible, so long as adequate addressing means (e.g., a data file coordinated with array feature layout) is provided.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

Biopolymer arrays can be fabricated by depositing previously obtained biopolymers (such as from synthesis or natural sources) onto a substrate, or by in situ synthesis methods. Methods of depositing obtained biopolymers include depositing drops onto a substrate from dispensers such as pin or capillaries (such as described in U.S. Pat. No. 5,807,522) or such as pulse jets (such as a piezoelectric inkjet head, as described in PCT publications WO 95/25116 and WO 98/41531, and elsewhere). The substrate is generally coated with a suitable linking layer prior to deposition, such as with polylysine or other suitable coatings as described, for example, in U.S. Pat. No. 6,077,674 and the references cited therein. Additional references that describe aspects of our in situ and deposition systems for array fabrication include U.S. Pat. No. 6,242,266, U.S. Pat. No. 6,232,072, U.S. Pat. No. 6,180,351, U.S. Pat. No. 6,171,797, U.S. Pat. No. 6,323,043 and U.S. patent application Ser. No. 09/302,898 filed Apr. 30, 1999 by Caren, et al. The disclosures of all of the above references concerning array fabrication being incorporated herein by reference in their entireties.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). At least some of the array features will be separated by intervening spaces. Light attenuating features will be provided for at least some of those spaces, typically all of them.

In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). "Hybridizing" and "binding", with respect to polynucleotides, are used interchangeably.

A "sensor region" refers to a contiguous (e.g., circular, rectangular etc.) area in which the array spots, features or elements of interest, as defined above, are found. In SPR analysis, the back side of such features are illuminated.

Thus, the image(s) collected corresponds to the back side of the sensor or scan region. As such, the sensor regions correspond to those portion of the array from which the resulting light angle changes are gauged. A "Surface Plasmon Resonance sensor region" is a sensor region set upon a metal film backed by a substantially planar and transparent portion of substrate material.

An "array layout" refers to one or more characteristics of the features, such as probe feature or light-attenuating feature positioning on the substrate, one or more feature dimensions, and an indication of a moiety at a given location.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information in accordance with the invention. The minimum hardware of the computer-based systems typically comprises a central processing unit (CPU), input means, output means, and data storage means. A skilled artisan can readily appreciate that any one of the currently available computer-based system are suitable for use in embodiments in accordance with the invention. The data storage means may comprise any manufacture comprising a recording of the information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

In describing the invention in greater detail than provided in the Summary and as informed by the Background and Definitions provided above, details regarding implementation of the invention are first described as to array reading or scanning methodology and associated software/hardware. Next, specific array/array substrate configurations are described. This discussion is followed by a description of methods of using arrays in accordance with embodiments in accordance with the invention and kits for use in the same.

First, however, it is noted that the methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein. Further, reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation, and the term "consisting" or the phrase "consisting essentially of."

One aspect in accordance with the invention provides for arrays (via their substrate configurations) that are themselves adapted to provide for high-contrast SPR images. Another aspect in accordance with the invention involves such arrays and scanners adapted to work in conjunction with such arrays. All of the scanner hardware, associated hardware, software and methodology of use are covered by the invention. In a similar vein, the physical aspects, manner of making or producing arrays, reading them and results produced accordingly are included in accordance with the invention.

As to the specifics of the arrays, they include a substrate having sensor features set upon a metal film in a pattern with relatively less or non-reflective areas. The nature of light reflected off of or at the metal film due to target-probe binding provides the means of array data acquisition. The periodic structure of the array and resultant reflectance allows for distinguishing readings for corresponding array sensor regions. Further, it reduces signal noise by avoiding unintended reflectance being gathered by light sensor(s) from regions adjacent regions corresponding to array sensor regions. Thus, embodiments in accordance with the invention offer an array structure by which one may differentiate array element readings from each other and from the background while multiplexing sensor regions in numbers in quantities of up to 10, 20, 50, 100, 1000, 5000, 1000, 10,000 or even more—the only limitations being the resolution of the imaging equipment and the wavelength of light used. The latter consideration being relevant to any limiting diffractive effects.

Variations of embodiments in accordance with the invention are constructed in order to at least avoid direct reflection of light toward a detector from non-sensor areas. To do so, the substrate in those regions is adjacent to or includes features disrupting reflection (at least in the form of total internal reflection). The material set upon the substrate (or the substrate itself) may include geometric features to attenuate reflection for non-sensor regions. The material itself may be light absorbing. The features may be relatively large in scale or in the form of surface grating.

If grating is provided, it can be used for reducing total reflection of one or more monochromatic source signals individually. It may also find use in conjunction with broadband sources (together with filters and/or color discriminating detectors) in SPR signal discrimination on the basis of color.

In any case, it should be understood that combinations of reflection-attenuating features according to aspects in accordance with the invention are also possible. Typical permutations are presented herein.

Analysis Methodology

Multiplexing of SPR analysis is achieved in embodiments in accordance with the invention by virtue of features that allow for resolution of reflected light off of a thin metal layer (e.g., a gold layer) backing a plurality of array feature sensor regions. As noted above, the sensor regions set upon the metal backing are regarded herein as SPR sensor regions. Such elements are differentiated from each other as well as background noise by virtue of portions of the array substrate which do not achieve total internal reflection in the manner of light reflecting off of the SPR sensor regions.

By creating and providing an array structure with alternating reflecting and relatively less or non-reflective zones (especially in a periodic fashion), one can determine the power and angle of light reflected off the relevant portions of the substrate with comparative ease. As discussed above in introducing SPR analysis, information about how much binding has occurred at an array location correlates to reflected light angle and/or intensity as driven by the resultant mass concentration of bound molecules effecting resonance energy and—ultimately—light reflectance for areas of interest.

Figure 1:
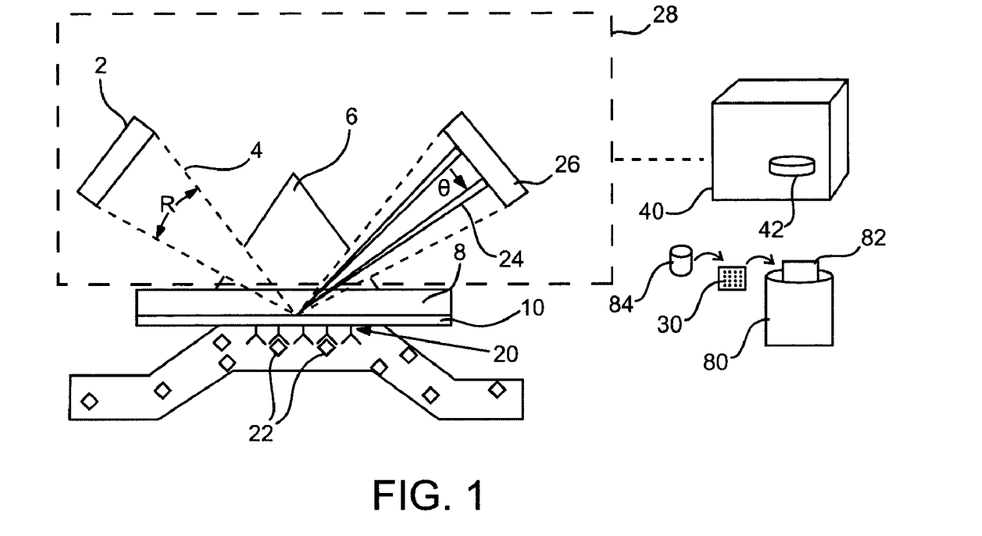
FIG. 1 shows an exemplary SPR setup for array analysis.

As shown in FIG. 1, light detection, any array movement, calculations and other activity typical to a scanner or reader 28 used to accomplish the task of obtaining data for an entire array is carried out under the control of electronic means such as a computer 40 under software control. Programming embodying the methodology may be loaded onto the reader/scanner computer, or the computer/microprocessor may be preprogrammed to run with the same. The programming can be recorded on computer readable media 42 (e.g., any medium that can be read and accessed directly by a computer). Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the database information.

A single region for SPR analysis is depicted in FIG. 1. Here, the elements of an SPR system are shown. A light source 2 is provided. By way of various optics, generally including a columnator, a beam 4 is directed toward a prism 6. The beam passes into and through an array substrate 8. Beam 4 undergoes total internal reflection within the substrate at its boundary with a thin metal coating 10 set upon the substrate's substantially planar surface in at least this region.

Array features 20 are bound or attached to the metal layer of the substrate.

Probes 22 are shown interacting with selected target array features. As a greater number of biomolecules become bound thereto, their mass concentration increases, resulting (for a given incident angle of light in an applied range of beam angles "R") in a light reflectance angle "θ" where light intensity maximizes, minimizes, or varies The resultant signal 24 is typically collected with a two-dimensional photo-detector such as a compound metal oxide semiconductor (CMOS) imager or a charge coupled device (CCD) imager. In this manner, data for an entire array or for selected sections of an array can be collected simultaneously.

Note, however, that especially where a small source beam is used, a reader or scanner 28 may be provided with movement stages (e.g., x-axis; y-axis) in order to use SPR to scan an array in raster fashion or otherwise. Furthermore, whether accomplished in such a manner or otherwise, taking multiple scans of an array may be useful for watching the time evolution of a signal.

In scanning, the wavelength of light selected is not usually critical. Yet, polarization should sometimes be adjusted to minimize the reflection signal in view of the fact that the reflected light is polarization dependent. Alternately, rather than polarizing the light source, one may opt to use polarization sensitive detection.

Arrays

Figure 2:
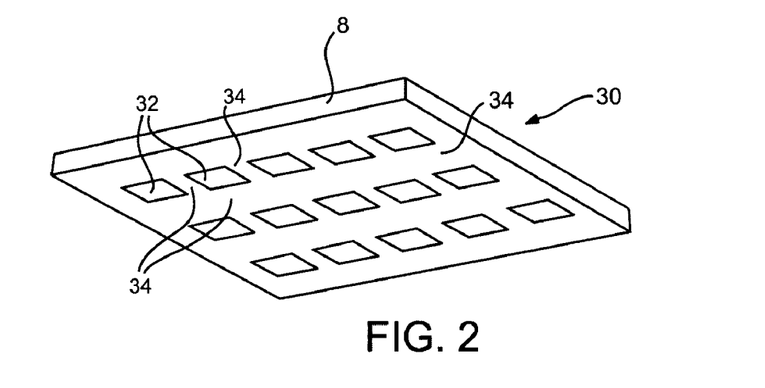
FIG. 2 shows an exemplary array as may be used in the setup shown in FIG. 1.

An exemplary array or portion of an array 30 is shown in FIG. 2. As described above, it includes a substrate 8. SPR sensing elements or regions 32 (having various probes set upon a thin metal film) are provided in a periodic fashion upon substantially planar portions of the substrate as may be noted by reference to the drawing. Of course, other patterns or periodic layouts may be used, just as the sensor regions may be shaped otherwise. However arranged, non-reflecting or poorly-reflecting separating regions 34 are provided between sensor features 32 areas. As commented upon above, these light-attenuating features or "means for light attenuation" allow for clearly distinguishing between the various SPR sensor elements off of which light is completely reflected—by virtue of the light and dark reflectance pattern gathered by sensor 26.

Figure 3A:
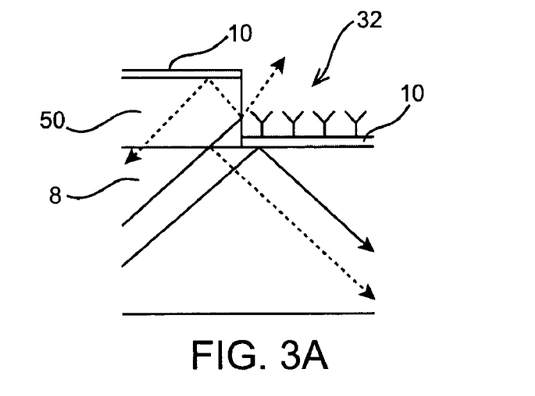
FIGS. 3A–3C show side-sectional views of an array embodiment in accordance with the invention using variations of a basic light attenuating structure.
Figure 3B:
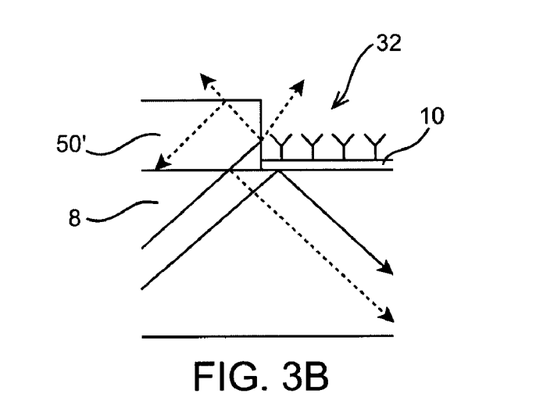
Figure 3C:
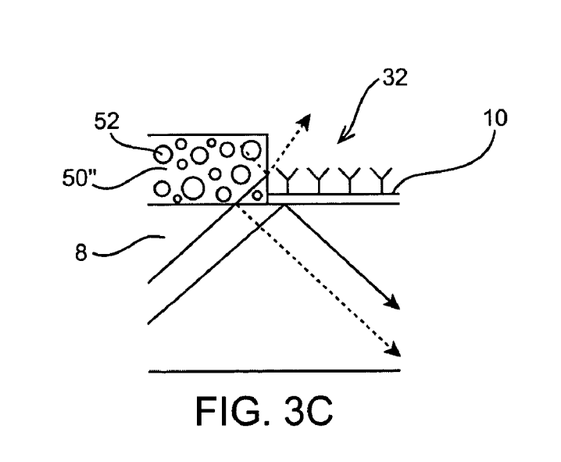

FIGS. 3A–3C show a most basic format for the light attenuating structures. These take the form of raised structures 50. The light attenuating structures are raised relative to the level of the substrate and/or the sensor region(s) defined thereon. Taller structures will tend to function so that light rays escape from their sides as depicted. With very tall raised structures, reflected light within the same may contact several walls (escaping to some degree each time), dissipating even more light that might be reflected toward sensor 26 as background. Suitable height (h) and width (w) of features will depend on the geometry selected. In a rectangular geometry, raised structure 50 would advantageously have a h/w ratio of about $\sin\beta/\sin(90-\beta)$, where $\beta$ is the incident angle of light to the surface normal of the substrate. As long as there is a detectable line of contrast between adjacent features 32, the width dimension is not critical. It may, however, generally be that the height dimension be on the order of about 1 to about 5 μm.

One manner of fabricating a raised light attenuating structure is to spin coat substrate 8 with a film of photo-patternable organic or inorganic polymer with a close index match to the substrate. After lithographic exposure, the film may be developed and a thin metal layer 10 such as gold evaporated or vapor deposited on the substrate. Even with the gold deposited everywhere, sufficient differential reflectivity to distinguish (at least the edges) of sensor regions 32 should be obtained with sufficiently tall raised portions 50. As indicated above, even taller structures will provide better contrast.

Structure 50' presented in FIG. 3B will, however, generally offer improved performance relative to that shown in FIG. 3A. Raised structure 50' lacks the reflective gold capping layer 10 set upon structure 50 as shown in FIG. 3A. As such, additional light is able to escape the light attenuating structure as depicted FIG. 3B. Though additional photolithographic steps are required, the raised structure shown in FIG. 3B is easily produced by simply patterning the gold layer before patterning the top layer defining structure 50'.

In FIG. 3C the raised layer 50" contains pigments or dies 52 that absorb light from the source. The choice of die or pigment will be dependent upon the substrate media and wavelength(s) of light selected. Generally, the dyes/pigments should be ones with high absorptivity, "ε". Depending on the efficacy of the light absorbance media included in the material, geometry to trap the light may be of lesser importance to achieve desired results than in the variations of the invention in FIGS. 3A and 3B. As illustrated, light that does not escape from the sides of the raised structure may simply be absorbed.

Figure 4A:
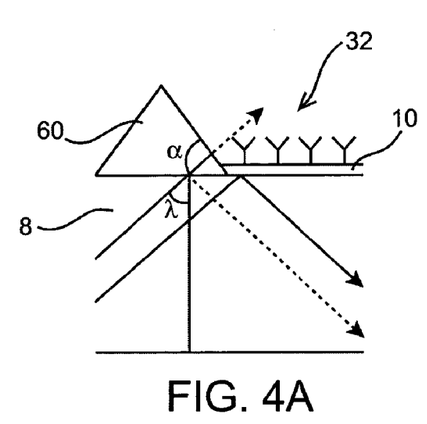
FIGS. 4A and 4B show side-sectional views of alternate geometries for large-scale light attenuating structures.
Figures 4B, 6:
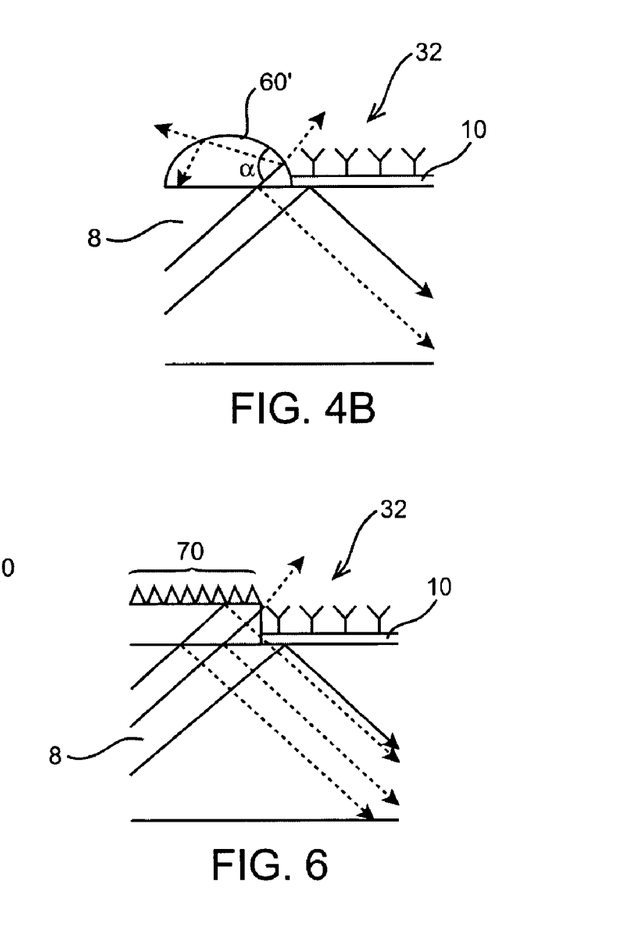
FIG. 6 shows a combination-type light attenuating structure combining such features as provided in FIGS. 3A–3C with that of FIG. 5.

FIGS. 4A and 4B illustrate further means of light attenuation. Raised surface features 60 and 60' are provided in shapes that are adapted to facilitate light ray exit by providing a greater incident angle "α" at which contact is made with the light-attenuating features. Typically, the shape and entry angle of the light are such that the exiting light is at an angle α that is substantially normal (90°) to the surface, thus minimizing back reflection.

Yet, since it may often be the case that incident light is scanned across a range of angles, the exit angle will only be normal at one such angle. Accordingly, the precise shape of the light-attenuating features should be configured to account for where one expects the strongest evanescent coupling to the analytes. Thus, α will have an optimum value of (90°−λ) as shown in FIG. 4A.

FIG. 4A illustrates a triangular cross-sectional shape 60 with it edge angled with respect to the plane of the substrate (i.e., it is not set substantially square or perpendicular thereto); FIG. 4B shows a structure with a curved cross-sectional shape 60'. Other shapes that will work in like manner (at least in comparison to a simple raised or 90° rectilinear structure as shown in FIGS. 3A–3B) include parabolic, semi-cylindrical, semi-spherical, pyramidal, and saw-toothed configurations. Others may be used as well. In any case, these features are advantageously employed in conjunction with the pigmenting approach mentioned above.

Figure 5:
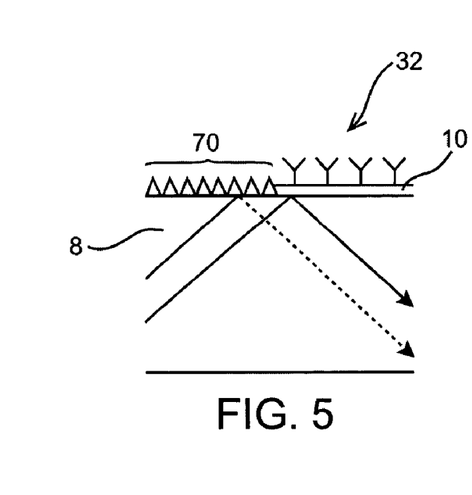
FIG. 5 shows a smaller-scale light attenuating structures than those presented in the previous figures.

In another implementation of the invention, surface gratings 70 are provided for light attenuation. Basically, these features serve as a roughened surface that "leak" out undesired light. Conveniently, the gratings may be patterned directly on the substrate between array elements. Naturally, the pitch of the grating selected will depend on the wavelength of light chosen for scanning.

Alternatively (as shown in FIG. 6), the gratings may be set upon a raised layer 50. In such cases, the top grating 70 will function much as in the situation of FIG. 5, whereas the sides of spacer 50 will function as noted above with respect to FIGS. 3A, 3B and/or 3C. This combination of reflected light attenuating features should offer improvement in contrast between sensing element regions and background noise from adjacent areas.

Yet, in some instances, it will be red to use gratings alone as shown in FIG. 5 since they may be produced without any deep etching or building-up of relatively tall structures that can be costly and/or time consuming to produce. Further, with a grating-only approach, it is feasible to illuminate with a monochromatic light source and look for the resultant regions of different color on the reflected pattern. In this way, one may follow the change in refractive index as correlated to analyte binding to probes by observing the movement of different color spots.

Any of a number of manufacturing techniques may be employed in producing the subject arrays. Of course, MEMS and nanofabrication techniques as noted above may be employed. In some cases, molding, hot embossing, casting or stamping techniques may also, or alternatively be also used.

In any case, it is noted that the geometric light-attenuating features need not be provided by a overlay of a matching or lower refractive index material to a substrate base. Indeed, in some instances, the substrate, including the light-attenuating features, may originally be formed in one piece of material. In which case, after the monolithic structure is formed, one may then deposit the requisite metal layer(s) and biopolymeric agent(s). Still further, it is contemplated that the arrays of the invention may be formed by attaching a plurality of pre-shaped parts together.

Regardless of the constructional techniques, features of the invention will be the subject of routine design optimization. Namely specifications such as the number of features, precise shape, pitch between features, height of the features, aspect rations and compositions of materials will be selected so as to be compatible with the chemistries introduced and collateral hardware—including the fluid delivery scheme.

Utility

The subject biopolymer optical scanners find use in a variety applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface at the sensor areas 34 is then detected via SPR.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids (or other molecules) that are complementary to probe sequences attached to the array surface. The presence of hybridized complexes is then detected.

Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference. Where the arrays are arrays of polypeptide binding agents (e.g., protein arrays), specific applications of interest include analyte detection/proteomics applications, including those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In any case, results from reading an array may be raw results (such as intensity readings for each feature in one or more color channels) or may be processed results such as obtained by applying saturation factors to the readings, rejecting a reading for a feature which is above or below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, Internet, etc. Alternatively, or in addition, the data representing array results may be stored on a computer-readable medium of any variety such as noted above or otherwise. Retaining such information may be useful for any of a variety of reasons as will be appreciated by those with skill in the art.

Kits

Kits for use in connection with the subject invention may also be provided. Such kits typically include at least a computer readable medium including instructions and programming embodying or adapted to direct the functionality as discussed above. The instructions may include software installation or setup directions. The instructions may include directions for directing the scanner to perform as desired. Typically, the instructions include both types of information.

Providing the software and instructions as a kit may serve a number of purposes. As shown in FIG. 1, the combination may be packaged in a wrapper 80 and purchased as a means of upgrading an existing scanner. The full program or some portion of it (typically at least such code as defining the subject methodology—alone or in combination with the code already available) may be provided as an upgrade patch. Alternately, the combination may be provided in connection with a new scanner in which the software is preloaded on the same. In which case, the instructions may serve as a reference manual (or a part thereof) and the computer readable medium as a backup copy to the preloaded utility.

In other instances, kits in accordance with the invention will include at least one of the arrays 30 as described above in a wrapper 80. Especially in the kits including one or more arrays, it may be desired to further include one or more additional components necessary for carrying out an analyte detection assay, such as one or more sample preparation reagents, buffers and the like. As such, the kits may include one or more containers 84 such as vials or bottles, with each container containing a separate component for the assay, and reagents for carrying out an array assay such as a nucleic acid hybridization assay or the like. The kits may also include buffers (such as hybridization buffers), wash mediums, enzyme substrates, reagents for generating a labeled target sample such as a labeled target nucleic acid sample, negative and positive controls. As above, written instructions—but this time for using the array assay devices for carrying out an array based assay—may be provided in the kit.

Any instructions are generally recorded on a suitable recording medium. For example, the instructions may be printed on a substrate, such as paper or plastic, etc. As such, the instructions may be present in the kits as a package insert 82, in the labeling of the container of the kit or components thereof (i.e., associated with the packaging or subpackaging), etc. In other embodiments, the instructions are present as an electronic storage data file present on a suitable computer readable storage medium 42, e.g., CD-ROM, diskette, etc., including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Of course, some form of access security or identification protocol may be used to limit access to those entitled to use the subject invention. As with the instructions, the means for obtaining the instructions and/or programming is generally recorded on a suitable recording medium.

Though the invention has been described in reference to certain examples, optionally incorporating various features, the invention is not to be limited to that specifically described. It is to be understood that the breadth of embodiments in accordance with the invention are to be limited only by the literal or equitable scope of the following claims.

It is evident from the above discussion that the above-described invention provides an effective and readily applicable way to improve the precision and extend the lifetime of optical scanners.

All publications and patents cited in this specification are herein incorporated by reference as if each individual publication or patent were specifically and individually indicated to be incorporated by reference. The citation of any publication is for its disclosure prior to the filing date and should not be construed as an admission that the embodiments in accordance with the invention are not entitled to antedate such publication by virtue of prior invention.

While specific embodiments in accordance with the invention have been described, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope in accordance with the invention. All such modifications are intended to be within the scope of the claims appended hereto. Stated otherwise, no exclusion of coverage of the claims made hereafter is intended by virtue of the embodiments in accordance with the invention provided.

What is claimed is:

1. A chemical probe array comprising: a substrate having a surface with a plurality of chemical probe Surface Plasmon Resonance sensor regions separated from each other by light-attenuating regions, wherein at least some of said light-attenuating regions comprise structures that are raised relative to a level of said Surface Plasmon Resonance sensor regions and are free of a metal capping film, and wherein said array is adapted for multiplexed Surface Plasmon Resonance detection of surface binding on said array.

2. The array of claim 1, wherein said light-attenuating regions are means for light attenuation.

3. The array of claim 1, wherein said raised structures include a light-absorbance material that is other than a metal capping film.

4. The array of claim 1, wherein said raised structures are angled or curved with respect to said Surface Plasmon Resonance sensor regions.

5. The array of claim 1, wherein at least 10 Surface Plasmon Resonance sensor regions are provided.

6. The array of claim 1, wherein said raised structures are capped by non-metallic grating.

7. The array of claim 1, wherein the chemical of the array is a biopolymer selected from polypeptides and nucleic acids.

8. A method of multiplexed surface Plasmon Resonance analysis comprising:
    contacting a sample suspected of comprising an analyte with a chemical array, wherein said array is adapted for multiplexed Surface Plasmon Resonance, said array comprising
        a substrate,
        a plurality of sensor regions, and
        a plurality of interfeature light-attenuating regions between said sensor regions to produce a pattern in reflected light, wherein at least some of said interfeature light-attenuating regions comprise structures that are raised relative to a level of said Surface Plasmon Resonance sensor regions and are free of a metal capping film;
    directing light at the array;
    collecting reflected light; and
    determining the presence of said analyte in said sample based on the nature of the reflected light.

9. The method of claim 8, wherein said analyte is selected from polypeptides and nucleic acids.

10. The method of claim 8, wherein the method further comprises a data transmission act in which a result from said determining the presence of said analyte is transmitted from a first location to a second location.

11. The method of claim 10, wherein said second location is a remote location.

12. A computer-readable medium comprising at least a portion of a program adapted to direct the method of claim 8.

13. The computer-readable medium of claim 12, wherein the entirety of said program is provided on said computer-readable medium.

14. A kit comprising the computer readable medium of claim 12, in packaged combination with instructions for use with the same.

15. A computer-readable medium containing data representing array results, wherein said data is produced according to the method of claim 8.

16. A kit comprising an array according to claim 1 and at least one of instructions for carrying out an assay or at least one container including reagents for carrying out an assay.

* * * * *